United States Patent
Wickersheim et al.

(10) Patent No.: US 11,109,742 B2
(45) Date of Patent: Sep. 7, 2021

(54) MAGNETIC COUPLING

(71) Applicant: Scholly Fiberoptic GmbH, Denzlingen (DE)

(72) Inventors: Johannes Wickersheim, Malterdingen (DE); Jochen Dietrich, Elzach (DE); Mateusz Cichosz, Freiburg (DE); Massimo Kubon, Emmendingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 336 days.

(21) Appl. No.: 16/168,043

(22) Filed: Oct. 23, 2018

(65) Prior Publication Data
US 2019/0117048 A1  Apr. 25, 2019

(30) Foreign Application Priority Data
Oct. 25, 2017 (DE) .................. 102017124981.8

(51) Int. Cl.
*A61B 1/00* (2006.01)
*G02B 23/24* (2006.01)

(52) U.S. Cl.
CPC ...... *A61B 1/00158* (2013.01); *A61B 1/00064* (2013.01); *A61B 1/00179* (2013.01); *A61B 1/00183* (2013.01); *A61B 1/00188* (2013.01); *G02B 23/2438* (2013.01); *G02B 23/2484* (2013.01); *A61B 1/00112* (2013.01)

(58) Field of Classification Search
USPC ..................................... 310/105, 103, 95, 92
See application file for complete search history.

(56) References Cited

U.S. PATENT DOCUMENTS

| | | | |
|---|---|---|---|
| 5,270,600 A | 12/1993 | Hashimoto | |
| 5,633,555 A * | 5/1997 | Ackermann | F04D 13/027 310/103 |
| 6,099,467 A * | 8/2000 | Kehr | A61B 1/00188 359/822 |
| 6,522,477 B2 * | 2/2003 | Anhalt | A61B 1/00096 359/694 |

(Continued)

FOREIGN PATENT DOCUMENTS

| | | |
|---|---|---|
| DE | 19713276 | 10/1998 |
| DE | 102010024003 | 12/2011 |

(Continued)

*Primary Examiner* — John P Leubecker
*Assistant Examiner* — Shankar Raj Ghimire
(74) *Attorney, Agent, or Firm* — Volpe Koenig

(57) ABSTRACT

A magnetic coupling is provided having two rings that are arranged concentrically in relation to one another, which are each mounted to be rotatable in relation to one another. An arrangement of at least three magnetic dipoles is respectively arranged on both rings, the magnetic dipoles facilitating magnetic coupling of the rings and a transmission of torque from a driving ring to a driven ring of the two rings. The magnetic dipoles of the arrangements at the driven ring and/or at the driving ring is/are aligned such that two like magnetic poles, which adjoin one another on the respective other ring, are always followed by an unlike magnetic pole, and the magnetic poles adjoining one another at the respective other ring are arranged in a manner corresponding to one another such that the two rings are magnetically coupled in an equilibrium position.

21 Claims, 2 Drawing Sheets

(56) References Cited

U.S. PATENT DOCUMENTS

| | | | | |
|---|---|---|---|---|
| 6,632,173 | B1* | 10/2003 | Kehr | A61B 1/00188 348/E5.027 |
| 8,343,042 | B2* | 1/2013 | Leiner | A61B 1/00158 600/167 |
| 8,821,385 | B2* | 9/2014 | Naito | A61B 1/01 600/114 |
| 9,510,744 | B2 | 12/2016 | Schrader et al. | |
| 9,924,854 | B2* | 3/2018 | Iwasaki | H04N 5/2254 |
| 10,653,301 | B2* | 5/2020 | Iguchi | A61B 1/0019 |
| 2003/0184179 | A1* | 10/2003 | Galbraith | H02K 39/00 310/166 |
| 2009/0051235 | A1* | 2/2009 | Brown | H02K 7/025 310/74 |
| 2010/0001592 | A1* | 1/2010 | Kawano | A61B 1/00158 310/12.14 |
| 2010/0286791 | A1* | 11/2010 | Goldsmith | A61B 17/0057 623/23.7 |
| 2011/0031837 | A1* | 2/2011 | Kuritani | F04C 15/0069 310/103 |
| 2011/0127869 | A1* | 6/2011 | Atallah | H02K 49/06 310/94 |
| 2013/0049367 | A1* | 2/2013 | Adachi | F01C 1/16 290/52 |
| 2014/0058203 | A1* | 2/2014 | Naito | A61B 1/00158 600/137 |
| 2014/0128674 | A1* | 5/2014 | Wieters | H01F 7/0252 600/109 |
| 2014/0163664 | A1* | 6/2014 | Goldsmith | A61B 17/12181 623/1.11 |
| 2015/0087998 | A1* | 3/2015 | Czupalla | A61B 5/0077 600/476 |
| 2015/0157307 | A1* | 6/2015 | Su | A61B 17/0293 600/208 |
| 2015/0200582 | A1* | 7/2015 | Headstrom | A61C 17/3445 310/25 |

FOREIGN PATENT DOCUMENTS

| | | |
|---|---|---|
| DE | 102015002372 | 8/2016 |
| WO | 9109223 | 6/1991 |

* cited by examiner

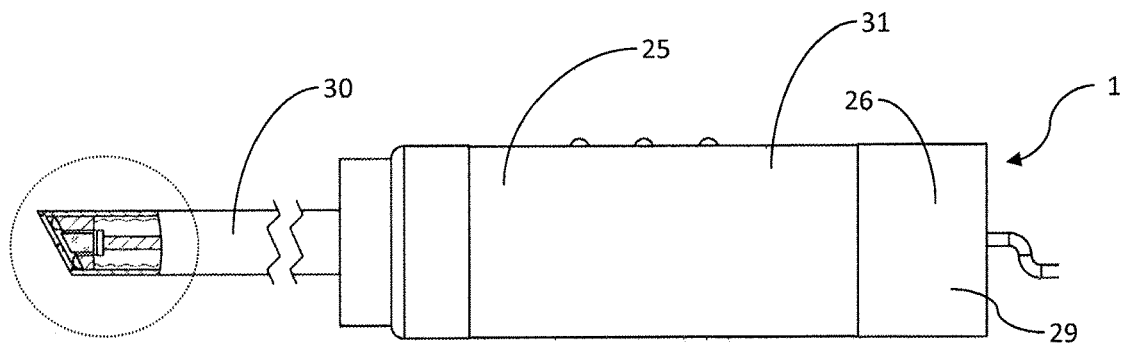
Fig. 1
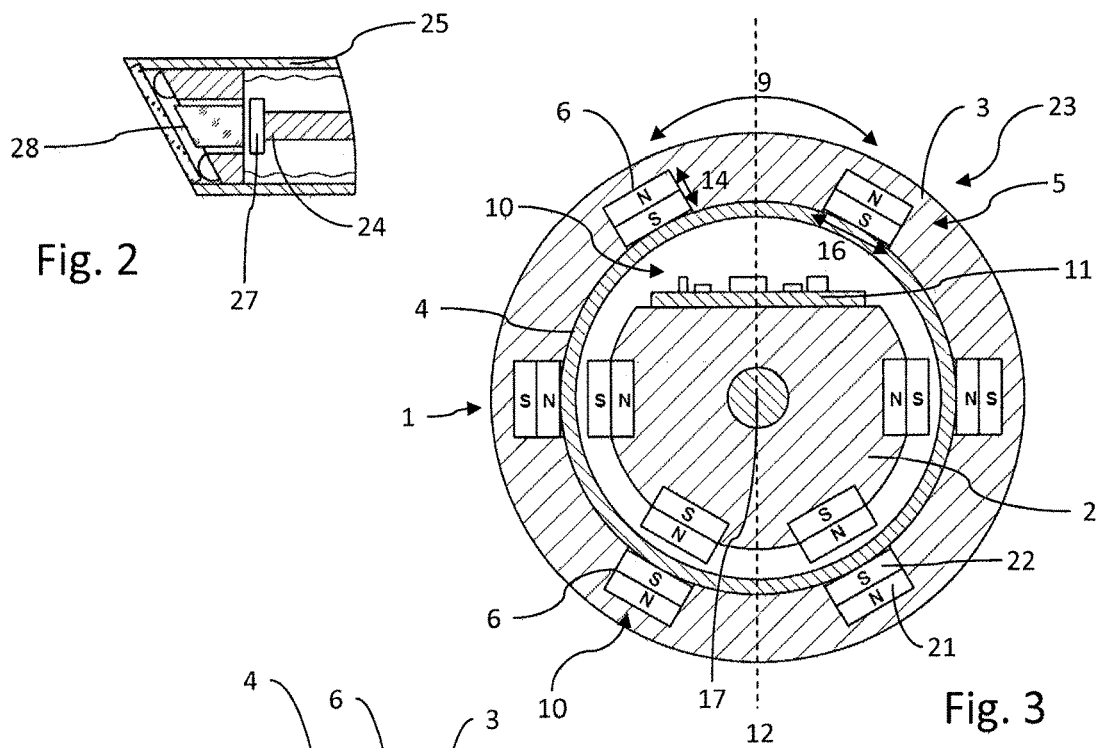
Fig. 2
Fig. 3
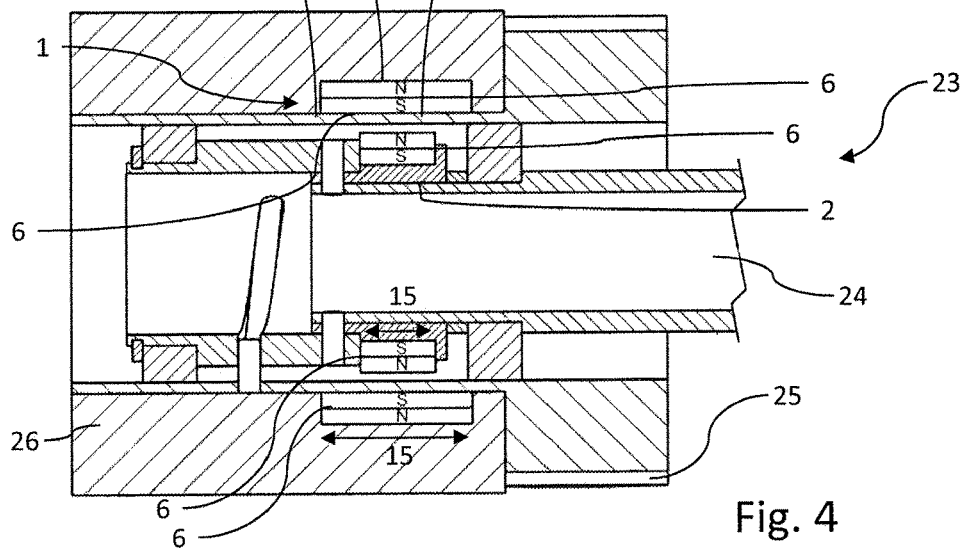
Fig. 4

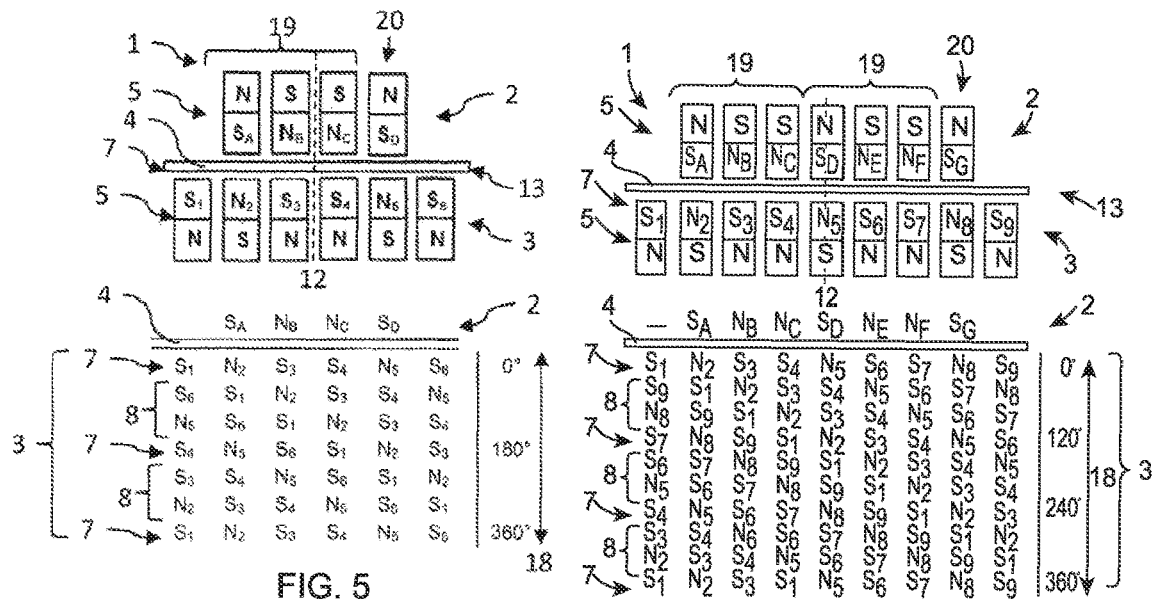
FIG. 5
FIG. 6
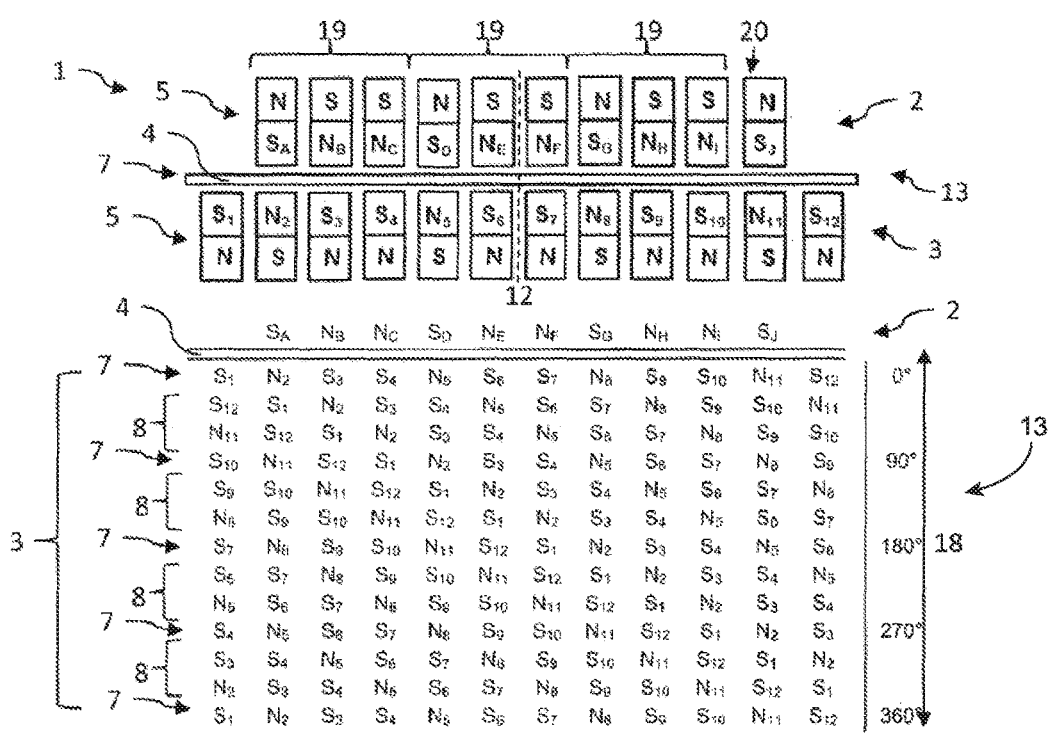
FIG. 7
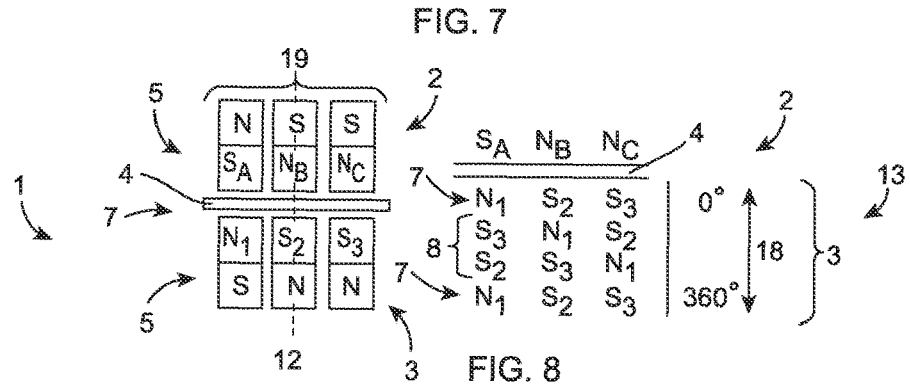
FIG. 8

MAGNETIC COUPLING

INCORPORATION BY REFERENCE

The following documents are incorporated herein by reference as if fully set forth: German Patent Application No. DE 10 2017 124 981.8, filed Oct. 25, 2017.

BACKGROUND

The invention relates to a magnetic coupling with two rings that are arranged concentrically in relation to one another, which are each mounted to be rotatable in relation to one another, and with a wall that is arranged between the rings, wherein the rings each have an arrangement of magnetic dipoles, wherein a transmission of a torque between the rings is possible through the separating wall as a result of magnetic coupling of the magnetic dipoles. In particular, provision can be made for the rings that are arranged concentrically in relation to one another to be formed as an outer ring and an inner ring, which is preferably arranged within the outer ring.

By way of example, such couplings are known from endoscopes or camera heads, in which a rotational movement for aligning an image sensor must be transferred through a separating wall, in particular a hermetically sealed separating wall. This is expedient for keeping an alignment of the image sensor fixed in space so that the observation horizon of a user does not change when the hermetic separating wall is rotated by the user for the purposes of changing the viewing direction of the endoscope. In the process, it is possible, for example, for an optical unit, which defines the direction of view, i.e. the field of view, of the endoscope, to be co-rotated with the hermetic separating wall.

Until now, achieving such magnetic couplings by a sequence of magnetic dipoles, for example embodied as permanent magnets, has been known, said sequence having either a sequence of like poles or an alternating sequence of mutually alternating poles on the facing side at each of the two rings and having a corresponding arrangement of dipoles on the respective other ring.

However, this is disadvantageous in that fitting together of the rings is possible in a plurality of rotational movements. By way of example, when the driven ring puts up a certain resistance against being driven by the driving ring, the magnetic coupling between the rings can consequently jump by an equilibrium position or a rest position, and so an image horizon definition is no longer unique and the endoscope is no longer present in the calibration state.

SUMMARY

Therefore, there is the object of developing a magnetic coupling of the type set forth at the outset, which overcomes the specified disadvantages.

This object is achieved by one or more features of the invention. In particular, according to the invention, the suggestion for achieving the object in the case of a magnetic coupling of the type described at the outset consequently is that at least one rest position and at least two repulsion positions of the rings are defined by a sequence of the magnetic dipoles of the arrangement, wherein the at least two repulsion positions are arranged next to one another in the rotational direction and follow the at least one rest position. What this achieves is that an excessively deflected driven ring is conveyed back into the preferred alignment again such that, for example, instances of magnetic decoupling of the magnetic coupling caused by frictional resistances are compensable, in particular automatically compensable. By way of example, should frictional resistances occur, the magnetic coupling according to the invention can prevent the magnetic coupling of the magnetic dipoles from releasing and the magnetic dipoles attracting one another in an undesired new coupling position such that, in such an alignment, the original rest position has been left. Furthermore, this can prevent the image horizon of an image sensor, for example, changing by a rotation of an endoscope housing since a compensation movement and a torque transmission through the separating wall are possible by the magnetic coupling.

Therefore, the invention renders it possible for at least one rest position and two repulsion positions to be definable proceeding from the arrangement of the dipoles on a first and a second ring. In the position defined to be a rest position, the magnetic dipoles of the first ring are present in a manner corresponding to the magnetic dipoles of the second ring such that an attractive magnetic force acts between the two rings. In the case of a rotation of the first ring relative to the second ring, a restoring force arises, said restoring force arising from the sum of the repulsive and attractive magnetic forces between the dipoles of the first and the second ring and restoring the rings relative to one another into the rest position.

Preferably, provision is even made for all or substantially all relative positions of the rings in relation to one another, apart from the rest position, to be repulsion positions. This simplifies the assembly of the rings in the correct orientation.

According to an advantageous development, provision can be made for the number of magnetic dipoles of the respective arrangements of magnetic dipoles of the rings to be the same or differ. Particularly preferably, the outer ring has more magnetic dipoles than the inner ring. In particular, the number of magnetic dipoles on the inner ring has been increased by one or two dipoles on the outer ring. As a result, additional clear space can be created on the inner ring. The magnetic dipoles can be embodied as permanent magnets.

As an alternative or in addition thereto, provision can be made for at least one dipole space of a ring not to have a magnetic dipole such that this at least one dipole space does not contribute to the magnetic attraction or repulsion force between the dipoles of the rings. Thus, a dipole gap may be formed at a free dipole space. Consequently, a vacancy is formable in the sequence of the dipoles. It was found that all or substantially all relative positions of the rings in relation to one another apart from the rest position being repulsion positions can be achievable more easily by way of such a vacancy. What can be particularly preferred here is if two adjacent dipole spaces of a ring respectively have no magnetic dipole. It may be furthermore preferable here if at least one dipole space has no magnetic dipole at the ring embodied as an inner ring. It may be particularly expedient here if at least one element of the group of electronic and/or mechanical functional units is arranged in free dipole spaces. In this way, it is possible to create installation space for an electronic and/or mechanical functional unit, with the functionality of the magnetic coupling not being impaired.

It may be particularly advantageous if respectively identical rotational angles are included between the dipole spaces of the two rings. Preferably, a rotational angle between the dipole spaces is at least 30°, in particular at least 40°, preferably at least 60°, further preferably 120°. By setting the undertaken rotational angles, it is possible to be able to ensure an arrangement that is fixed in space and/or secured against rotation of a functional unit connected to an inner ring.

According to a further advantageous configuration, provision can be made for the number of magnetic dipoles on a first ring of the two rings, in particular on an outer ring, to be odd or even. As an alternative or in addition thereto, provision can further be made for the number of magnetic dipoles on a second ring of the two rings, in particular on an inner ring, to be odd or even. It is particularly preferable for the number of magnetic dipoles on both rings to be either even or odd. As result of this teaching, a large number of functioning arrangements is producible. Here, the number of dipoles can also be determined by the size of the available magnets and the size of the integration space. What applies here, as a matter of principle, is that a combinatorial reliability of an encoding increases with an increasing number of magnetic dipoles contained in a system.

In such a configuration, it may be particularly expedient if, in the case of an odd number of magnetic dipoles on one ring or on both rings, a dipole represents a center of symmetry or an axis of symmetry for a mirror symmetry and/or wherein, in the case of an even number of dipoles on one ring or on both rings, a center of symmetry or an axis of symmetry lies between two adjacent dipoles. Here, it may be particularly expedient for this type of symmetry to be determinable if the sequence of the magnetic dipoles is represented in linear notation. As a result of the symmetry in the sequence of the magnetic dipoles of the arrangement, it is possible to produce particularly many possible sequences of magnetic dipoles, by means of which a repulsive force, and consequently a return into the rest position, is causable on account of the arrangement of the dipoles in relation to the rest position. As a result, it is possible to better prevent jumping over a rest position into a possibly further present rest position.

In order to be able to form a magnetic coupling that is as space saving as possible but nevertheless as stable as possible, it may be advantageous if the magnetic dipoles are respectively aligned radially at or on the rings.

As an alternative or in addition to the aforementioned configuration, provision may be made according to a further advantageous configuration for the magnetic dipoles to have such a flat embodiment that a height, which corresponds to an axial extent of a magnetic dipole, is less than a length and/or a width of the magnetic dipoles, in particular wherein the length extends in the axial direction in relation to an axis of rotation of the rings and/or wherein the width extends in a rotational direction of the rings. As a result, a structure that is as compact as possible is achievable, wherein a sufficiently high magnetic force is producible between the dipoles of the first and of the second ring in order to be able to undertake a torque transmission. Here, provision can be made for a mutual distance between adjacent dipoles, which are arranged on the inner ring or the outer ring, to be greater than the distance between two dipoles lying opposite one another in the rest position. Here, one of the two opposing dipoles is respectively arranged on the outer ring and one of the two dipoles is respectively arranged on the inner ring. Consequently, there preferably is magnetic coupling of the opposing magnetic dipoles in the rest position.

According to a further advantageous configuration, provision can be made for the at least one rest position to be configured by virtue of more magnetic dipoles of the rings attracting one another than repelling one another in this position. An attraction or repulsion between the rings emerges from a sum of the individual magnetic forces, which act between the rings between the adjacent magnetic dipoles in the respective position. Therefore, in a rest position of the magnetic coupling, more unlike adjacent magnetic poles of the magnetic dipoles of the rings are present than like adjacent magnetic poles. In this context, the term magnetic poles relates to a north pole or a south pole of the magnetic dipoles.

As an alternative or in addition thereto, provision can be made according to a further advantageous configuration for the at least two repulsion positions to be configured by virtue of more magnetic dipoles of the rings repelling one another than attracting one another in each of these positions. Preferably, provision can be made, in the process, for more adjacent magnetic poles of the rings to be like than unlike such that, due to a repulsive magnetic force, in particular the sum of the individual magnetic forces that act between the dipoles of the two rings, there is a return from one of the repulsion positions into at least one rest position.

According to a further advantageous configuration, provision can be made for the magnetic coupling to have a plurality of rest positions, wherein at least two repulsion positions are formed in each case between two rest positions. In particular, provision can be made here for the magnetic coupling to have at least two or at least three rest positions. In order to better prevent jumping over a rest position into a further rest position, it may be expedient here if an identical rotational angle lies between the rest positions, said rotational angle preferably being 90° or 120° or 180°.

As an alternative or in addition thereto, provision can be made according to a further advantageous configuration for a rotational angle of at least 30°, in particular at least 40°, preferably at least 60°, further preferably 120°, to be provided between the at least two adjacent repulsion positions. Consequently, it is possible to prevent repositioning of the magnetic coupling from a first rest position into a second rest position setting in particularly well in the case of an occurrence of a relative rotation between the two rings.

In order to be able to better protect components arranged within the separating wall from external influences, it may be expedient if the separating wall hermetically isolates the two rings from one another. As an alternative or in addition thereto, it may likewise be expedient for the separating wall to have an electrically insulating configuration such that no electric currents are able to flow through the separating wall from the inner ring to the outer ring.

In order to be able to avoid an incorrect position of the magnetic coupling, for example by jumping over a rest position into a further rest position, it may be expedient according to a further advantageous configuration for the arrangement of magnetic dipoles of the two rings to each have a basic building block or a plurality of basic building blocks, wherein the magnetic poles, adjoining the further rings, of the magnetic dipoles of the basic building block have at least one of the following sequences: south pole (S), north pole (N), north pole (N) and/or north pole (N), south pole (S), south pole (S) and/or north pole (N), north pole (N), south pole (S) and/or south pole (S), south pole (S), north pole (N). It was found that this allows basic building blocks to be providable, by which it is possible to construct dipole arrangements with the described advantages. Here, or in general, provision can be made for the magnetic dipoles of the basic building blocks of the two arrangements to correspond to one another in the rest position such that two adjoining basic building blocks of the two rings attract one another.

According to a further advantageous configuration, provision can be made for at least one of the two arrangements of magnetic dipoles of the two rings to have at least one filler building block in addition to at least one, or the at least one, basic building block, wherein the magnetic poles, adjoining the further of the two rings, of the magnetic dipoles of the filler building block have the following sequence: north pole (N) and/or south pole (S) and/or north pole (N), north pole (N) and/or south pole (S), south pole (S) and/or north pole (N), south pole (S) and/or south pole (S), north pole (N) and/or wherein the magnetic dipoles of the filler building blocks of the two arrangements correspond to one another in the rest position such that two adjoining filler building blocks of the two rings attract one another.

As an alternative or in addition thereto, it may be advantageous if the filler building block has a non-magnetic configuration. In this configuration form, a similar coupling is developed as in the case of unoccupied dipole spaces, at which no magnetic dipole is arranged. Therefore, a non-magnetic filler building block cannot contribute to the magnetic attraction or repulsion force between the outer ring and the inner ring.

According to further advantageous configuration, provision can be made for at least one of the two arrangements of magnetic dipoles of the two rings to be assembled in such a way that the magnetic poles thereof, adjoining the further of the two rings, of the magnetic dipoles are arranged in the following sequence or a portion of the sequence of at least three dipoles: S, N, S, S, N, S, S, N, S, S, N, S or N, S, N, N, S, N, N, S, N, N, S, N and/or for the magnetic dipoles, adjoining this sequence or the portion, of the second arrangement to be aligned corresponding thereto such that the magnetic dipoles of the two adjacent arrangements of the two rings attract one another in the rest position.

Moreover, the invention relates to an endoscope having a coupling according to one or more features of the invention, as described herein.

According to an advantageous configuration of the endoscope, it is suggested that the endoscope comprises an inner body, wherein the inner body is separated from a housing by way of the separating wall, wherein the inner body is rotatably mounted relative to the housing, in particular at an inner side of the separating wall, and comprises an actuation apparatus, which is magnetically coupled or coupleable to the inner body by way of the magnetic coupling, wherein the inner body is rotatable relative to the housing by way of a rotation of the actuation apparatus relative to the housing, in particular in such a way that the inner body is able to be set in a manner fixed in space and/or in a manner secured against rotation in the case of a rotation of the housing. As a result, it is possible to keep the inner body stationary and rotate the housing at the same time.

It may be particularly preferred if an image sensor is arranged on the inner body, in particular in an endoscope-tip region, and if an optical unit, in particular an input optical unit, is arranged or formed at the housing such that, in the case of a rotation of the housing for the purposes of changing a field of view, the optical unit is movable therewith, wherein the image sensor is able to be set in a manner fixed in space and/or in a manner secured against rotation by way of a rotation of the actuation apparatus relative to the housing. Therefore, the image sensor can remain approximately stationary in this case while the optical unit is correspondingly rotated. Here, a user can change the field of view of the optical unit without the image horizon co-rotating in the process.

According to an advantageous configuration, provision can be made for the endoscope to comprise a focusing apparatus for setting a zoom factor and/or an image focus, said focusing apparatus being magnetically coupled or coupleable to the inner body by way of the magnetic coupling. This is advantageous in that, for example, a stop of an adjustment mechanism remains perceivable over the magnetic coupling.

The invention moreover relates to a special use of a magnetic coupling, as described herein, for aligning an image sensor, in particular for setting a relative rotation of an image sensor, for example the aforementioned image sensor, in relation to an optical unit, for example the aforementioned optical unit, in particular in relation to an input optical unit, of an endoscope.

Furthermore, the invention also relates to the use of a magnetic coupling, as described herein, for defining an assembly position of an inner body within a, or the, housing. This renders an incorrect relative orientation of the two rings of the magnetic coupling being inadvertently implemented during the assembly avoidable. Here, an increased number of repulsion positions following the rest position on both sides, i.e., in the case of a rotation of the rings relative to one another in both senses of rotation, is more advantageous.

Furthermore, the invention also relates to the use of a magnetic coupling, as described herein, for setting an optical parameter of an, or the, optical unit, in particular for setting a zoom factor and/or a focus position. The term zoom factor may relate to an image magnification. The term focus position can relate to a focus setting and/or focusing of an object.

Thus, the invention relates to a magnetic coupling with two rings that are arranged concentrically in relation to one another, which are each mounted to be rotatable in relation to one another, wherein an arrangement of at least three magnetic dipoles is respectively arranged on both rings, said magnetic dipoles facilitating magnetic coupling of the rings and a transmission of torque from a driving ring to a driven ring of the two rings, wherein the magnetic dipoles of the arrangements at the driven ring and/or at the driving ring is/are aligned in such a way that two like magnetic poles, which adjoin one another on the respective other ring, are always followed by an unlike magnetic pole, and wherein the magnetic poles adjoining one another at the respective other ring are arranged in a manner corresponding to one another such that the two rings are magnetically coupled in an equilibrium position. Preferably, the driving ring is configured as an outer ring and the driven ring is configured as an inner ring.

BRIEF DESCRIPTION OF THE DRAWINGS

Now, the invention will be described in more detail on the basis of a plurality of illustrated exemplary embodiments; however, it is not restricted to these exemplary embodiments. Further exemplary embodiments arise by combining the features of individual claims or of a plurality of claims amongst themselves and/or with individual features or a plurality of features of the exemplary embodiments.

Shown in detail are:

FIG. 1 shows an embodiment of an endoscope according to the invention in a schematic illustration, which is shown in part as a longitudinal section in the region of the endoscope tip, FIG. 2 shows a detailed view of the endoscope-tip region circled by the dashed line in FIG. 1, FIG. 3 shows a cross section through the magnetic coupling of the endoscope according to FIG. 1 in a schematic illustration, FIG. 4 shows a longitudinal section through the actuation and/or focusing apparatus and the shaft of the endoscope according to FIG. 1, FIG. 5 shows a sequence of magnetic dipoles of two possible arrangements of the two rings, wherein the sequence of the magnetic dipoles at the inner ring is shown above the separating wall and the sequence of the magnetic dipoles at the outer ring is shown below the respective separating wall, and a table, belonging to the individual arrangements, with the various positions of the magnetic coupling, which are able to be set by setting the rotational angles, wherein the arrangement at the inner ring is comprised of four magnetic dipoles and the arrangement at the outer ring is comprised of six magnetic dipoles, FIG. 6 shows a further sequence of magnetic dipoles of two possible arrangements of the two rings, wherein the sequence of the magnetic dipoles at the inner ring is shown above the separating wall and the sequence of the magnetic dipoles at the outer ring is shown below the respective separating wall, and a table, belonging to the individual arrangements, with the various positions of the magnetic coupling, which are able to be set by setting the rotational angles, wherein the arrangement at the inner ring is comprised of seven magnetic dipoles and the arrangement at the outer ring is comprised of nine magnetic dipoles, FIG. 7 shows a further sequence of magnetic dipoles of two possible arrangements of the two rings, wherein the sequence of the magnetic dipoles at the inner ring is shown above the separating wall and the sequence of the magnetic dipoles at the outer ring is shown below the respective separating wall, and a table, belonging to the individual arrangements, with the various positions of the magnetic coupling, which are able to be set by setting the rotational angles, wherein the arrangement at the inner ring is comprised of ten magnetic dipoles and the arrangement at the outer ring is comprised of twelve magnetic dipoles, and FIG. 8 shows a further sequence of magnetic dipoles of two possible arrangements of the two rings, wherein the sequence of the magnetic dipoles at the inner ring is shown above the separating wall and the sequence of the magnetic dipoles at the outer ring is shown below the respective separating wall, and a table, belonging to the individual arrangements, with the various positions of the magnetic coupling, which are able to be set by setting the rotational angles, wherein the arrangement at the inner ring is comprised of three magnetic dipoles and the arrangement at the outer ring is composed of three magnetic dipoles.

DETAILED DESCRIPTION

FIGS. 1 to 3 show an endoscope according to the invention, or portions thereof are shown, wherein the endoscope as a whole is denoted by 23. The endoscope 23 comprises a shaft 30 and a hand piece 31.

The endoscope 23 comprises a magnetic coupling according to the invention, the latter being denoted as a whole by 1 and being arranged within the hand piece 31.

The magnetic coupling 1 has two rings 2, 3 that are arranged concentrically in relation to one another, wherein a first ring thereof is configured as an inner ring 2 and a second ring thereof is configured as an outer ring 3. The inner ring 2 has an external diameter that is smaller than the internal diameter of the outer ring 3 and it is arranged within the outer ring 3.

The two rings 2, 3 are respectively mounted in rotatable fashion in relation to one another, with a separating wall 4 being arranged between the rings 2, 3. The separating wall 4 can separate the two rings 2, 3 hermetically and/or electrically from one another. The inner ring 2 and the outer ring 3 are respectively mounted at the separating wall 4 in rotatable fashion. The separating wall 4 consists of a material through which magnetic field lines can pass.

Both rings 2, 3 each have an arrangement 5 of a plurality of magnetic dipoles 6. In the embodiment according to FIG. 3, the outer ring 3 has six magnetic dipoles 6 and the inner ring 2 has four magnetic dipoles 6. In a rest position 7, in which the magnetic dipoles 6 of the two rings 2, 3 are magnetically coupled to one another, a transmission of a torque to the inner ring 2 through the separating wall 4 is possible when the outer ring 3 is rotated, and so said inner ring 2 can be rotated with the outer ring 3, particularly in synchronous fashion. The rest position 7 corresponds to an equilibrium position.

At least one rest position 7 and at least two repulsion positions 8 of the rings 2, 3 are defined by a certain sequence of the magnetic dipoles 6 of the arrangement 5. Here, the at least two repulsion positions 8 are arranged next to one another in the rotational direction 9 and they follow the at least one rest position 7. A magnetic coupling 1 may have a plurality of rest positions 7, with the above-described basic design merely repeating in the process.

In the embodiment of the endoscope 23 according to the invention as per FIG. 3, a magnetic coupling 1 is configured with two rest positions 7 and four repulsion positions 8. The inner ring 2, which is configured as part of an inner body 24 of the endoscope 23 in this case, has a total of six dipole spaces 10, with only four of the dipole spaces 10 being occupied by respectively one magnetic dipole 6. A rotational angle 18 of 60 degrees is included in each case between the individual dipole spaces 10 of the two rings 2, 3. Two adjacent dipole spaces 10 on the inner ring 2 are not occupied by a magnetic dipole 6, and so these dipole spaces 10 do not contribute to the magnetic attraction or repulsion force between the magnetic dipoles 6 of the rings 2, 3. An electronic functional unit 11, such as a printed circuit board, for example, is arranged on the free dipole spaces 10 of the inner ring 2. Thus, installation space that can be used for arranging further components, such as functional units, is created by the free dipole spaces 10. Consequently, a compact design of the endoscope 23 is nevertheless possible.

The respective sequence of the magnetic dipoles 6 of the two arrangements 5 from FIG. 3 is reproduced in FIG. 5 in linear notation 13, with the arrangement 5 being "cut" at one place in this case. Therefore, the respective outer ends are immediately adjacent in the actual circular arrangement. As may be gathered from the table likewise illustrated in FIG. 5, a rest position 7 is present in the case of a relative rotation of the inner ring 2 in relation to the outer ring 3 by 180 degrees in each case. The magnetic dipoles 6 of the inner ring 2 and of the outer ring 3 are arranged adjacently to one another in the rest position 7 in such a way that their magnetic poles 21, 22 adjoining one another are unlike. Therefore, a south pole (S) 22 rests against a north pole (N) 21 in the rest position 7, and vice versa. Consequently, all magnetic dipoles 6 of the two rings 2, 3 attract in the rest position, and so a greatest possible magnetic attraction between the rings 2, 3 arises from the sum of magnetic attraction and repulsion forces in this position. This also applies to the further possible configurations of a magnetic coupling 1 that are shown in FIGS. 5 to 8. By way of example, as may be read from the table in FIG. 5, the rest positions 7 of the magnetic coupling 1 arise at a rotational angle 18 of 0 degrees, 180 degrees and 360 degrees.

In the case of a relative rotation of the two rings 2, 3 into a repulsion position 8, more like magnetic poles 21, 22 than unlike magnetic poles 21, 22 of the magnetic dipoles 6 of the two rings 2, 3 adjoin one another. By way of example, as may be read from the table in FIG. 5, the repulsion positions 8 of the magnetic coupling 1 arise at a rotational angle 18 of 60 degrees, 120 degrees, 240 degrees and 300 degrees. If there is such a relative rotation of the two rings 2, 3 into a repulsion position 8, there is a return into a rest position 7 that is driven by the magnetic repulsion force. Therefore, the sum of the repulsive magnetic forces between the magnetic dipoles 6 in a repulsion position 8 is greater than the sum of the attractive magnetic forces.

The arrangement 5 of the magnetic dipoles 6 has a symmetric configuration. Since there is an even number of magnetic dipoles 6 on the inner ring 2 and on the outer ring 3, an axis of symmetry 12 for a mirror symmetry lies between two adjacent magnetic dipoles 6.

In order to be able to achieve a configuration of the magnetic coupling 1 that saves as much space as possible, the magnetic dipoles 6 of the two rings 2, 3 are aligned radially such that respectively one magnetic pole 21, 22 of each dipole 6 of the inner ring 2 adjoins the outer ring 3 and/or respectively one magnetic pole 21, 22 of each dipole 6 of the outer ring 3 adjoins the inner ring 2.

A particularly space-saving configuration of the magnetic coupling 1 is achieved by virtue of a height 14, which corresponds to an axial extent of a magnetic dipole 6, being less than a length 15 and/or a width 16 of the magnetic dipoles 6. Here, the length 15 extends in the axial direction in relation to an axis of rotation 17 of the rings 2, 3 and the width 16 extends in a rotational direction 9 of the rings 2, 3. The length 15 of the magnetic dipoles 6 at the outer ring 3 is greater than the length 15 of the magnetic dipoles 6 at the inner ring 2. This renders it possible to keep the necessary installation space at the inner ring 2 as small as possible and nevertheless set a magnetic force between the dipoles that suffices to facilitate a torque transmission.

Provision can likewise be made for not all magnetic dipoles 6 to attract in a rest position 7 of the magnetic coupling 1 and/or for not all magnetic dipoles 6 to repel in a repulsion position 8 of the magnetic coupling 1. What is decisive here is that an attractive force emerges from the sum of all repulsive and attractive magnetic forces between the magnetic dipoles 6 of the two rings 2, 3 in the rest position 7 and/or that a repulsive force emerges from the sum of all repulsive and attractive magnetic forces between the magnetic dipoles 6 of the two rings 2, 3 in the repulsion position 8—particularly in comparison with the rest position.

FIGS. 5 to 8 show a plurality of sequences of possible arrangements 5 of magnetic dipoles 6 of magnetic couplings 1. Here, this is purely an exemplary list, which should not be understood to be conclusive.

The configurations of magnetic couplings 1 shown in FIGS. 5 to 7 each have a plurality of rest positions 7, respectively two repulsion positions 8 being arranged between said rest positions 7. On the inner ring 2, two dipole spaces 10, in particular adjacent dipole spaces, are respectively not occupied by magnetic dipoles 6.

The magnetic coupling 1 of FIG. 6 consists of an arrangement 5 of seven magnetic dipoles 6 at the inner ring 2 and an arrangement 5 of nine magnetic dipoles 6 at the outer ring 3. It has three rest positions 7, between which a rotational angle 18 of 120 degrees is included in each case.

The magnetic coupling 1 of FIG. 7 consists of an arrangement 5 of ten magnetic dipoles 6 at the inner ring 2 and an arrangement 5 of twelve magnetic dipoles 6 at the outer ring 3. It has four rest positions 7, between which a rotational angle 18 of 90 degrees is included in each case.

In the case of the magnetic coupling 1 of FIG. 8, an arrangement 5 of respectively three magnetic dipoles 6 is provided both at the inner ring 2 and at the outer ring 3. Therefore, the magnetic coupling 1 only has one rest position 7, and so a complete rotation through 360 degrees in the rotational direction 9 is required to bring it back into the rest position 7.

The arrangements 5 of magnetic dipoles 6 of the two rings 2, 3 according to FIGS. 5 to 8 are constructed in each case from at least one basic building block 19, wherein the magnetic poles 21, 22, adjoining the respective other ring 2, 3, i.e., either a north pole 21 or a south pole 22, of the magnetic dipoles 6 of the basic building block 19 have at least one of the following sequences: south pole (S), north pole (N), north pole (N) and/or north pole (N), south pole (S), south pole (S) and/or north pole (N), north pole (N), south pole (S) and/or south pole (S), south pole (S), north pole (N). Here, the magnetic dipoles 6 of the basic building blocks 19 of the two arrangements 5 correspond to one another in the rest position 7 such that two adjoining basic building blocks 19 of the two rings 2, 3 attract one another.

In the case of arrangements 5 made of more than three magnetic dipoles 6, further dipole spaces 10 can be filled using a filler building block 20. In the case of arrangements 5 with a number of dipole spaces that represent a multiple of three, the dipole spaces 10 are preferably occupied by further elementary building blocks 19. In the case of a number of dipole spaces 10 that is unequal to a multiple of three, the diode spaces 10 should be occupied by at least one filler building block 20 in addition to at least one elementary building block 19. The magnetic poles 21, 22, adjoining the further of the two rings 2, 3, i.e., either a north pole 21 or a south pole 22, of the magnetic dipoles 6 of the filler building block 20 can have the following sequence: north pole (N) and/or south pole (S) and/or north pole (N), north pole (N) and/or south pole (S), south pole (S) and/or north pole (N), south pole (S) and/or south pole (S), north pole (N). The magnetic dipoles 6 of the filler building blocks 20 of the two arrangements 5 are arranged corresponding to one another in the rest position 7 such that two adjoining filler building blocks 20 of the two rings 2, 3 attract one another.

In general, it is possible to state that the arrangements 5 at the inner ring 2 and/or at the outer ring 3 are constructed in such a way that two like magnetic poles are always followed by an unlike magnetic pole.

The endoscope 23 further comprises an inner body 24, which forms the inner ring 2 or on which the inner ring 2 is arranged. The outer ring 3 is connected to an actuation apparatus 26 and/or a focusing apparatus 29, or formed by the latter. The inner body 24 is separated from a housing 25 and/or from the actuation apparatus 26 by the separating wall 4 of the magnetic coupling 1. At an inner side of the separating wall 4, the inner body 24 is rotatably mounted relative to the housing 25 and/or relative to the outer ring 3, in particular relative to the actuation apparatus 26 and/or focusing apparatus 29. The actuation apparatus 26 and/or focusing apparatus 29 is rotatably mounted at an outer side of the separating wall 4. The separating wall 4 is connected to the housing 25 or formed by the housing 25. Moreover, the actuation apparatus 26 and/or the focusing apparatus 29 is/are rotatably mounted relative to the housing.

The inner body 24 is magnetically coupled or coupleable to the actuation apparatus 26 and/or the focusing apparatus 29 by way of the magnetic coupling 1. Therefore, the inner body 24 is able to always be set in the same position, while the housing 25 is rotatable. By rotating the actuation apparatus 26 and/or the focusing apparatus 29, it is possible to co-rotate the inner body 24 in a synchronous fashion.

An optical unit 28, which is also adjustable during a rotation of the housing 25, is arranged at the housing 25, in particular at the shaft 30, in an endoscope-tip region. Hence, the field of view of the optical unit 28 is able to be set by way of a rotation of the housing 25. Consequently, a compensation rotation by way of the actuation apparatus 26 is possible during a rotation of the housing 25 in order to keep an image sensor 27, which is arranged on the inner body 24 and likewise arranged in the endoscope-tip region, in a manner fixed in space and/or secured against rotation. Here, it is possible to transmit torque from the actuation apparatus 26 onto the inner body 24.

Furthermore, the actuation apparatus 26 can be configured, alternatively or in addition thereto, as a focusing apparatus 29 or the endoscope 23 can comprise a focusing apparatus 29 in addition to the actuation apparatus 26. A zoom factor and/or an image focus is able to be set by way of the focusing apparatus 29. Here, it is likewise possible to transmit a torque from the focusing apparatus 29 onto the inner body 24.

LIST OF REFERENCE SIGNS

1 Magnetic coupling
2 Inner ring
3 Outer ring
4 Separating wall
5 Arrangement of magnetic dipoles
6 Magnetic dipole
7 Rest position
8 Repulsion position
9 Rotational direction
10 Dipole space
11 Electronic functional unit
12 Axis of symmetry
13 Linear notation
14 Height of the magnetic dipole
15 Length of the magnetic dipole
16 Width of the magnetic dipole
17 Axis of rotation of the rings
18 Rotational angle
19 Basic building block
20 Filler building block
21 North pole
22 South pole
23 Endoscope
24 Inner body
25 Housing
26 Actuation apparatus
27 Image sensor
28 Optical unit
29 Focusing apparatus
30 Shaft
31 Hand piece

The invention claimed is:

1. A magnetic coupling (1), comprising:
two rings (2, 3) that are arranged concentrically in relation to one another, and mounted to be rotatable in relation to one another;
a separating wall (4) arranged between the rings (2, 3);
an arrangement (5) of magnetic dipoles (6) on each of the two rings (2, 3);
wherein a transmission of a torque between the rings (2, 3) is carried out through the separating wall (4) by a magnetic coupling of the magnetic dipoles (6);
at least one rest position (7) and at least two repulsion positions (8) of the rings (2, 3) are defined by a sequence of the magnetic dipoles (6) of the arrangement (5);
the at least two repulsion positions (8) are arranged next to one another in a rotational direction (9) and follow the at least one rest position (7) such that two directly adjacent ones of the repulsion positions are defined; and
the at least two repulsion positions (8) are configured with more of the magnetic dipoles (6) of the rings (2, 3) repelling one another than attracting one another in each of said repulsion positions.

2. The magnetic coupling (1) as claimed in claim 1, wherein a number of the magnetic dipoles (6) arranged in dipole spaces of the respective arrangements (5) of magnetic dipoles (6) of the two rings (2, 3) differ, at least one free dipole space (10) is provided on at least one of the rings (2, 3) that does not have one of the magnetic dipoles (6) such that said at least one free dipole space (10) does not contribute to a magnetic attraction or repulsion force between the magnetic dipoles (6) of the rings (2, 3).

3. The magnetic coupling (1) as claimed in claim 2, wherein at least one element selected from the group of electronic or mechanical functional units (11) is arranged in the at least one free dipole spaces (10), and identical rotational angles (18) are included between the dipole spaces (10) of the two rings (2, 3).

4. The magnetic coupling (1) as claimed in claim 1, wherein at least one of a number of the magnetic dipoles (6) on a first ring (2, 3) of the two rings (2, 3), is odd or a number of the magnetic dipoles (6) on a second ring (2, 3) of the two rings (2, 3) is odd, and one of the magnetic dipoles (6) represents a center of symmetry or an axis of symmetry (12) for a mirror symmetry.

5. The magnetic coupling (1) as claimed in claim 1, wherein at least one of a number of the magnetic dipoles (6) on a first ring (2, 3) of the two rings (2, 3), is even or a number of the magnetic dipoles (6) on a second ring (2, 3) of the two rings (2, 3) is even, and a center of symmetry or an axis of symmetry (12) lies between two adjacent magnetic dipoles (6).

6. The magnetic coupling (1) as claimed in claim 1, wherein at least one of: the magnetic dipoles (6) are respectively aligned radially at or on the rings (2, 3) or the magnetic dipoles (6) are embodied flat with a height (14), which corresponds to an axial extent of a magnetic dipole (6), being less than at least one of a length (15) or a width (16) of the magnetic dipoles (6), wherein the length (15) extends in an axial direction in relation to an axis of rotation (17) of the rings (2, 3) and the width (16) extends in a rotational direction (9) of the rings (2, 3).

7. The magnetic coupling (1) as claimed in claim 1, wherein the at least one rest position (7) is configured by having more of the magnetic dipoles (6) of the rings (2, 3) attracting one another than repelling one another in said at least one rest position due to more adjacent magnetic poles (21, 22) of the rings (2, 3) being unlike than like, and due to the at least two repulsion positions (8) being configured with more of the magnetic dipoles (6) of the rings (2, 3) repelling one another than attracting one another in each of said repulsion positions and more of the magnetic dipoles of the rings (2, 3) being like than unlike a return is generated due to a repulsive magnetic force from one of the repulsion positions (8) into the at least one rest position (7).

8. The magnetic coupling (1) as claimed in claim 1, wherein the magnetic coupling (1) has a plurality of rest positions (7), and at least two repulsion positions (8) are formed in each case between two rest positions (7), and a rotational angle (18) that lies between each of the rest positions (7) is equal.

9. The magnetic coupling (1) as claimed in claim 1, wherein the separating wall (4) at least one of hermetically isolates or electrically insulates the two rings (2, 3) from one another.

10. The magnetic coupling (1) as claimed in claim 1, wherein the arrangement (5) of the magnetic dipoles (6) on each of the two rings (2, 3) each have at least one basic building block (19), magnetic poles (21, 22), adjoining the other ring (2, 3), of the magnetic dipoles (6) of one of the basic building blocks (19) have at least one of the following sequences: south pole (S), north pole (N), north pole (N); north pole (N), south pole (S), south pole (S); north pole (N), north pole (N), south pole (S); or south pole (S), south pole (S), north pole (N); and the magnetic dipoles (6) of the basic building blocks (19) of the arrangement (5) of the magnetic dipoles (6) on each of the two rings (2, 3) correspond to one another in the rest position (7) such that two adjoining basic building blocks (19) of the two rings (2, 3) attract one another.

11. The magnetic coupling (1) as claimed in claim 10, wherein at least one of the two arrangements (5) of the magnetic dipoles (6) of one the two rings (2, 3) has at least one filler building block (20) in addition to the at least one basic building block (19), and the magnetic poles (21, 22), adjoining an other of the two rings (2, 3), of the magnetic dipoles (6) of the filler building block (20) have the following sequence: north pole (N), south pole (S), north pole (N); north pole (N), south pole (S); south pole (S), north pole (N); south pole (S), south pole (S), north pole (N).

12. The magnetic coupling (1) as claimed in claim 11, wherein both of the arrangements (5) of the magnetic dipoles (6) of the two rings (2, 3) have at least one of the filler building blocks (20) in addition to the at least one basic building block (19), and the magnetic dipoles (6) of the filler building blocks (20) of the two arrangements (5) correspond to one another in the rest position (7) such that two adjoining filler building blocks (20) of the two rings (2, 3) attract one another.

13. The magnetic coupling (1) as claimed in claim 1, wherein at least one said arrangement (5) of the magnetic dipoles (6) on each of the two rings (2, 3) is assembled such that magnetic poles (21, 22) thereof, adjoining an other of the two rings (2, 3), of the magnetic dipoles (6) are arranged in the following sequence or a portion of the sequence of at least three dipoles (6): S, N, S, S, N, S, S, N, S, S, N, S or N, S, N, N, S, N, N, S, N, N, S, N' and wherein the magnetic dipoles (6), adjoining said sequence or the portion of the sequence, of an other of the at least two arrangements (5) of the other of the two rings (2, 3) are aligned corresponding thereto such that the magnetic dipoles (6) of the arrangement (5) of the magnetic dipoles (6) on each of the two rings (2, 3) which are adjacent to one another attract one another in the rest position (7).

14. An endoscope (23) with a magnetic coupling (1) as claimed in claim 1.

15. The endoscope (23) as claimed in claim 14, further comprising:
an inner body (24);
a housing, the inner body (24) being separated from the housing (25) by the separating wall (4);
the inner body (24) is rotatably mounted relative to the housing (25);
an actuator (26) which is magnetically coupled or coupleable to the inner body (24) by the magnetic coupling (1);
the inner body (24) is rotatable relative to the housing (25) by a rotation of the actuator (26) relative to the housing (25), and the inner body (24) is able to be set in a manner fixed in space, secured against a rotation of the housing (25).

16. The endoscope (23) as claimed in claim 15, further comprising:
an image sensor (27) arranged on the inner body (24);
an optical unit (28) arranged or formed at the housing (25) such that, during a rotation of the housing (25) for changing a field of view, the optical unit (28) is movable therewith; and
the image sensor (27) is settable in a manner fixed in space, secured against rotation, in the event of a rotation of the actuation apparatus (26) relative to the housing (25).

17. The endoscope (23) as claimed in claim 16, further comprising a focusing apparatus (29) for setting at least one of a zoom factor or an image focus, said focusing apparatus being magnetically coupled or coupleable to the inner body (24) by way of the magnetic coupling (1).

18. The endoscope (23) as claimed in claim 16, wherein the magnetic coupling aligns the image sensor (27) in relation to the optical unit (28).

19. The magnetic coupling (1) as claimed in claim 1, wherein the magnetic coupling is connected between an inner body and a housing to align an assembly position of the inner body (24) within the housing (25).

20. The magnetic coupling (1) as claimed in claim 1, wherein the two rings are an inner ring and an outer ring.

21. The magnetic coupling (1) as claimed in claim 1, wherein an excessively deflected driven ring is conveyed back into a preferred alignment in the at least one rest position by the two directly adjacent ones of the repulsion positions.

\* \* \* \* \*